United States Patent [19]
Ohyu

[11] Patent Number: 5,891,031
[45] Date of Patent: Apr. 6, 1999

[54] BIOMEDICAL MAGNETIC FIELD MEASURING APPARATUS HAVING DIFFERENT TYPES OF PICKUP COILS ARRANGED AT THE SAME POSITION AND INCLUDING CROSSTALK CORRECTION

[75] Inventor: Shigeharu Ohyu, Otawara, Japan

[73] Assignee: Kabushiki Kaisha Toshiba, Kawasaki, Japan

[21] Appl. No.: 718,869

[22] Filed: Sep. 24, 1996

[30] Foreign Application Priority Data

Sep. 25, 1995 [JP] Japan ................................. 7-246285

[51] Int. Cl.⁶ ..................................................... A61B 5/05
[52] U.S. Cl. ........................... 600/409; 600/544; 324/248; 324/244
[58] Field of Search ................................. 128/653.1, 733, 128/731, 898; 324/244, 246, 248, 260, 261, 245, 247, 254, 258; 600/409, 544, 546

[56] References Cited

U.S. PATENT DOCUMENTS

| | | | |
|---|---|---|---|
| 5,243,984 | 9/1993 | Ogura | 128/653.1 |
| 5,437,276 | 8/1995 | Takada | 128/653.1 |
| 5,444,373 | 8/1995 | Johnson | 324/248 |
| 5,451,871 | 9/1995 | Igarashi | 324/248 |

FOREIGN PATENT DOCUMENTS 5 297091  11/1993  Japan .

*Primary Examiner*—William E. Kamm
*Assistant Examiner*—Eleni Mantis Mercader
*Attorney, Agent, or Firm*—Oblon, Spivak, McClelland, Maier & Neustadt, P.C.

[57] ABSTRACT

The sensitivity in detection in a depth direction of a living body and the overall signal-to-noise ratio of an apparatus are improved, whereby a distribution of current sources in the living body or a plurality of current dipoles can be inferred more accurately than they conventionally are. A pickup coil array is made by combining a plurality of types of pickup coils that are mutually different in at least one of the order of a differential and a base line. The plurality of types of pickup coils are mutually different in, for example, only the order of a differential or only a base line, and are arranged separately at different measurement points or arranged at the same measurement point. Included is a magnetic source inferring means for inferably computing information on magnetic sources in a living body or information on the distribution of magnetic sources on the basis of detection signals provided by the plurality of types of pickup coils. The magnetic source inferring means includes a means for compensating for the influence of magnetic crosstalk among the plurality of types of pickup coils.

13 Claims, 15 Drawing Sheets

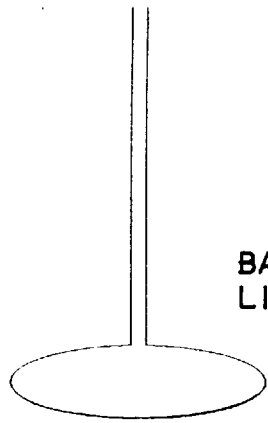
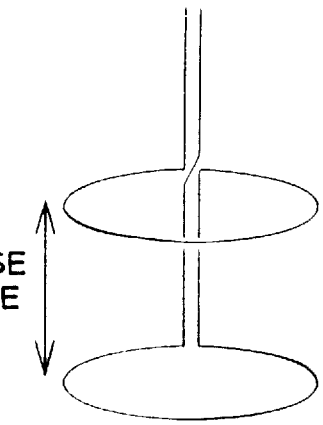
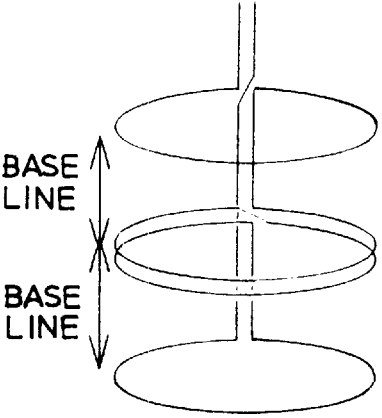
FIG. 2A
PRIOR ART
FIG. 2B
PRIOR ART
FIG. 2C
PRIOR ART
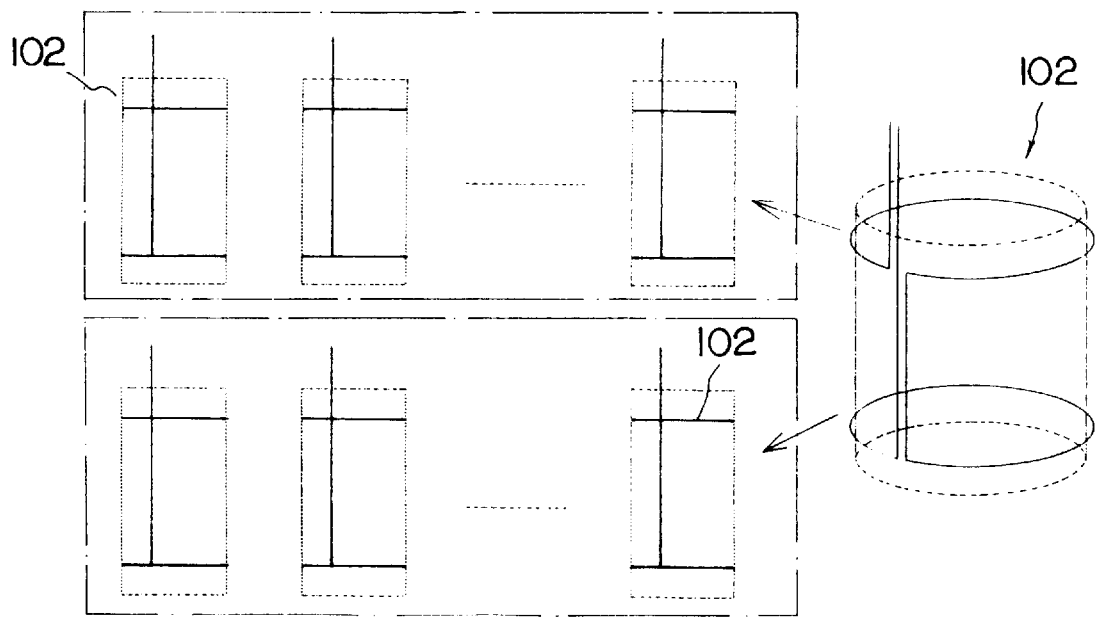
FIG. 3
PRIOR ART

5,891,031

BIOMEDICAL MAGNETIC FIELD MEASURING APPARATUS HAVING DIFFERENT TYPES OF PICKUP COILS ARRANGED AT THE SAME POSITION AND INCLUDING CROSSTALK CORRECTION

BACKGROUND OF THE INVENTION

1. Field of the Invention

The present invention relates to a biomedical magnetic field measuring apparatus. More particularly, this invention is concerned with a biomedical magnetic field measuring apparatus having a field detection unit in which a fragile magnetic field generated in a living body is sensed by a pickup coil and then led to a superconducting ring referred to as a superconducting quantum interference device (SQUID).

2. Description of the Related Art

In recent years, a SQUID fluxmeter serving as a biomedical magnetic field measuring apparatus in which superconducting quantum interference devices (SQUIDs) are used to measure magnetic fluxes in a living body has been put to practical use. The SQUID fluxmeter falls into a radiofrequency (rf)-SQUID type and direct current (dc)-SQUID type. The dc-SQUID type is used generally these days because sensitivity is excellent and few noises occur.

In the case of the dc-SQUID type, when a dc bias current of a level disabling retention of a superconducting state is supplied to a junction of a superconducting ring, if a magnetic field originating from a living body is detected using a pickup coil and led to the superconducting ring, a periodically-varying voltage to the detected magnetic field is induced in the junction. From this viewpoint, when the voltage in the junction varies, a magnetic flux canceling the variation is applied from a feedback coil to the superconducting ring so that a voltage proportional to a current flowing through the feedback coil can be read externally. A circuit thus configured is referred to as a flux locked loop (FLL) circuit. Owing to this circuit, an output proportional to a magnetic field detected by a pickup coil can be obtained.

A typical configuration of a pickup coil array employed in such a SQUID fluxmeter is shown in FIG. 1, and various forms of windings of pickup coils are shown in FIGS. 2A to 2C. A pickup coil array 100 shown in FIG. 1 has a plurality of first-order differential type pickup coils 101 arranged along a curved coil arrangement surface so that the axial-directions of the coils 101 will be substantially perpendicular to the surface of the head of a patient. This configuration is currently the mainstream of a SQUID fluxmeter. A magnetometer type pickup coil (the order of a differential is 0) shown in FIG. 2A, a first-order differential type pickup coil shown in FIG. 2B, and a second-order differential type pickup coil shown in FIG. 2C are used as the pickup coil 101. Above all, the second-order differential type pickup coil has the better ability to remove a magnetic field originating from an external noise than the first-order differential type coil, and is therefore employed in measuring a magnetic field in the environment with a larger external noise. The first-order differential type pickup coil has the poorer ability to remove an external noise and is therefore desirably used for measurement in a magnetic shielding room. The magnetometer type pickup coil does not have the ability to remove an external noise and is therefore unused in general. As shown in FIGS. 2B and 2C, a distance in axial direction between two coil loop planes is referred to as a base line. A conventional (differential type) pickup coil array is characterized by the fact that a plurality of pickup coils having the same base line are arranged on a curved coil arrangement surface. Incidentally, a third-order or higher-order differential type pickup coil in which consideration is taken into the durability to an external noise has been conceived.

It has been revealed that if information on current sources in a living body is inferred from the results of a measurement performed using a biomedical magnetic field measuring apparatus including a pickup coil array having the foregoing structure, there is the fear of bringing about drawbacks described below.

(1) When a distribution of current sources distributed in a living body three-dimensionally is inferred using a solution like a linear least squares method, a distribution of current sources that are distributed at shallower positions than they actually are is liable to be inferred.

(2) A plurality of current dipoles are imagined in a living body, if the positions, sizes, and orientations of the dipoles are inferred through non-linear optimization, small magnetic fields generated by dipoles located at deeper positions are hidden behind large magnetic fields generated by dipoles located at shallower positions. It is therefore hard to detect the dipoles at deeper positions accurately.

In an effort to solve this problem, a proposal has been made for a method in which a plurality of, for example, first-order differential type pickup coils 102 are, as shown in FIG. 3, arranged in steps in its axial direction, and information on current sources in a living body is inferred from magnetic field strengths detected by these pickup coils 102.

However, a magnetic field measuring apparatus including a pickup coil array having the structure described in conjunction with FIG. 3 has a problem that since a magnetic field in a living body detected by a pickup coil located away from the living body is small, the signal-to-noise ratio of a pickup coil located far away becomes inferior to that of a pickup coil located nearby. As a whole, a contribution is hardly made to improvement of accuracy in inference.

SUMMARY OF THE INVENTION

The present invention attempts to break through the foregoing situation. An object of the present invention is to provide a biomedical magnetic field measuring apparatus capable of inferring a distribution of current sources in a living body or a plurality of current dipoles therein more accurately than a known apparatus by improving the sensitivity in detection in a depth direction of a living body and the overall signal-to-noise ratio of the apparatus. More particularly, an object of the present invention is to provide a biomedical magnetic field measuring apparatus that when the position of a distribution of current sources distributed three-dimensionally is to be inferred, does not infer the position of the distribution as a shallower position than it actually is but can infer the position of the distribution accurately. Another object of the present invention is to provide a biomedical magnetic field measuring apparatus that when a plurality of current dipoles are to be inferred, if the plurality of current dipoles lie at different depths, can accurately infer even the dipoles located at deeper positions.

For accomplishing the foregoing objects, the present invention provides a biomedical magnetic field measuring apparatus having a pickup coil array in which pickup coils each sensing a magnetic flux originating from a magnetic source in a living body are arranged, wherein the pickup coil array is made by combining a plurality of types of pickup coils that are mutually different in terms of at least one of the order of a differential and the base line.

For example, the plurality of types of pickup coils are coils mutually different in terms of only the order of a differential or coils mutually different in terms of only the base line. Moreover, the plurality of types of pickup coils are arranged at different measurement points at which a magnetic flux is sensed. The plurality of types of pickup coils are arranged at the same measurement point at which the magnetic flux is sensed. The plurality of types of pickup coils are formed so that their coil loops close to a living body are located at the same or substantially the same position in the axial direction of the same bobbin.

More preferably, the biomedical magnetic field measuring apparatus includes a magnetic source inferring means for inferably computing a single magnetic source or a plurality of magnetic sources in a living body or information on a distribution of magnetic sources on the basis of signals sensed by the plurality of types of pickup coils. The magnetic source inferring means includes a means for compensating for the influence of magnetic crosstalk among the plurality of types of pickup coils.

BRIEF DESCRIPTION OF THE DRAWINGS

In the accompanying drawings:

FIGS. 2A to 2C show forms of windings of pickup coils in relation to the orders of a differential;

FIG. 3 shows another configuration of pickup coils in the known art;

DESCRIPTION OF THE PREFERRED EMBODIMENTS

Embodiments of the present invention will be described with reference to the drawings.

First Embodiment

The first embodiment of the present invention will be described in conjunction with FIGS. 4 to 11.

Figure 1:
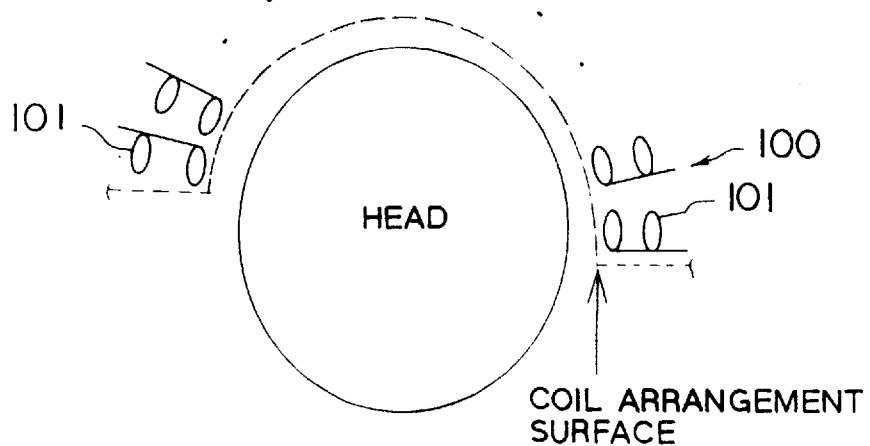
FIG. 1 is an explanation diagram concerning the configuration of a typical pickup coil array in a known art.
Figure 4:
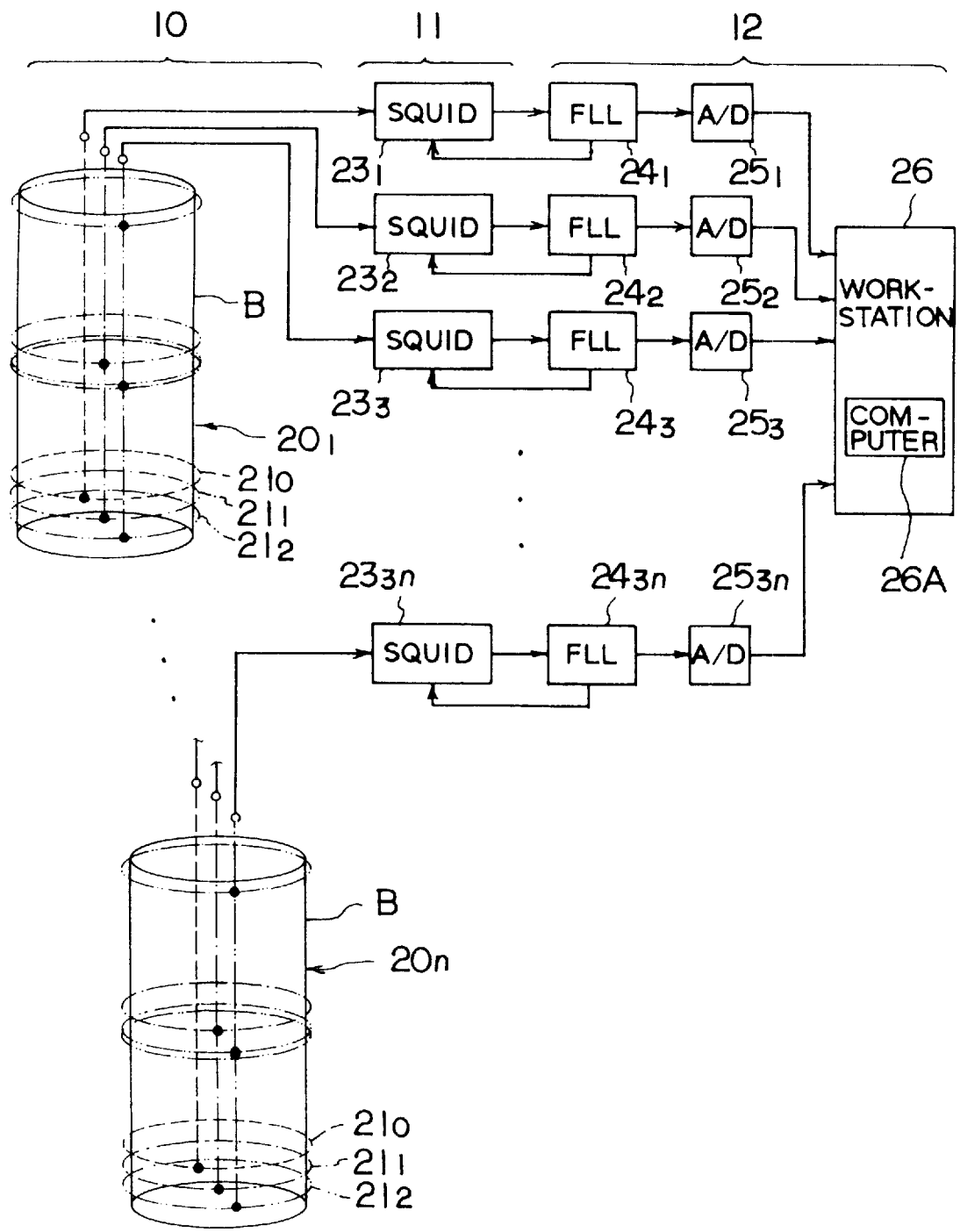
FIG. 4 is a schematic block diagram of a biomedical magnetic field measuring apparatus in accordance with the first embodiment of the present invention.

FIG. 4 is a schematic block diagram of a biomedical magnetic field measuring apparatus using a multi-channel dc-SQUID fluxmeter. The measuring apparatus comprises a pickup coil array 10, a SQUID unit 11, and a data processing unit 12. The pickup coil array 10 is composed of a plurality of pickup coil units $20_1$ to $20_n$. Each pickup coil unit $20_1$ (to $20_n$) is composed of a set of magnetometer type, first-order differential type, and second-order differential type pickup coils $21_0$, $21_1$, and $21_2$. The pickup coils $21_0$, $21_1$, and $21_2$ are, as illustrated, wound about the same bobbin B. Herein, the first-order differential type and second-order differential type pickup coils $21_1$ and $21_2$ shall have an equal base line.

Figure 5:
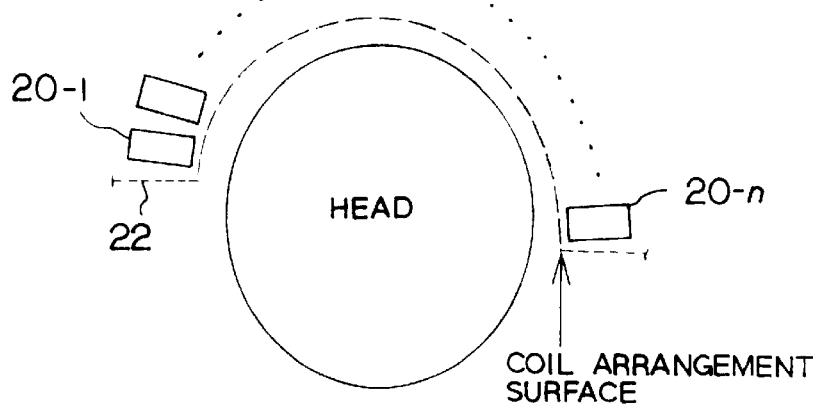
FIG. 5 is an arrangement explanation diagram for arranging pickup coils for studies of the head.

The pickup coil units $20_1$ to $20_n$ are, as shown in FIG. 5, stowed in a Dewar 22 having a coil arrangement surface curved along the skin surface of an object region of measurement of a living body (for example, the head), and arranged with the coil-axis directions thereof substantially perpendicular to the coil arrangement surface. The pickup coil units $20_1$ to $20_n$ are therefore placed three-dimensionally around the object region of measurement. At the same time, three types of pickup coils $21_0$, $21_1$, and $21_2$ of magnetometer, first-order differential, and second-order differential types are arranged at the same measurement point (a plurality of measurement points are present).

The SQUID unit 11 includes a plurality of SQUID circuits $23_1$ to $23_{3n}$ (three times larger than the number of pickup coil units) associated with the measurement points. The SQUID circuits $23_1$ to $23_{3n}$ are connected independently to the pickup coils $21_0$, $21_1$, and $21_2$ of the pickup coil units $20_1$ to $20_n$. Each of the SQUID circuits $23_1$ to $23_{3n}$ has a SQUID (superconducting quantum interference device) formed with a superconducting ring having two junctions, and leads magnetic fluxes detected by the pickup coils $21_0$ to $21_2$ to the junctions via input coils that are not shown. The SQUID unit 11 and pickup coil array 10 are stowed in the Dewar 22 in which they are cooled by liquid helium, and retained in a superconducting state.

The data processing unit 12 includes FLL circuits $24_1$ to $24_{3n}$ and A/D converters $25_1$ to $25_{3n}$ which are associated with detection channels, and also includes a workstation for data processing 26. The FLL circuits $24_1$ to $24_{3n}$ carry out a so-called flux locked loop (FLL) operation for providing a feeding back signal to an applied magnetic field so that a dc bias current can be supplied to the superconducting rings of the associated SQUID circuits $21_1$ to $23_{3n}$ or the voltages at the junctions of the superconducting rings will not vary. The fed-back signal outputs of the FLL circuits are provided as detection signals corresponding to magnetic fluxes to the A/D converters $25_1$ to $25_{3n}$ associated with the channels. The detection signals are digitized by the A/D converters $25_1$ to $25_{3n}$ and read by a computer 26A in the workstation 26.

Figure 6:
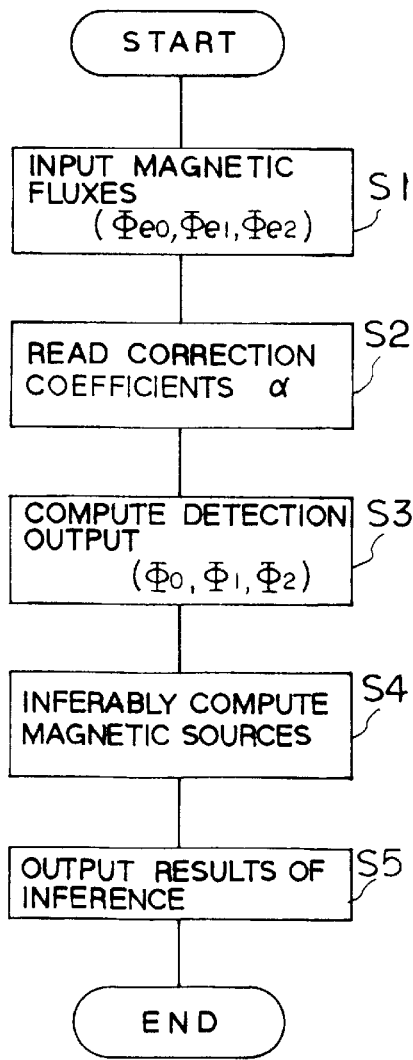
FIG. 6 is a flowchart briefly describing data computation by a computer in a workstation.

The computer 26A executes, for example, software shown in FIG. 6 according to the read detection signals associated with the channels.

When a plurality of pickup coils are arranged at the same measurement point as they are in this embodiment, since the pickup coils are mutually very close, magnetic crosstalk caused by the mutual inductance of the pickup coils poses a problem. In this embodiment, therefore, compensation such as the one described below is performed on the mutual inductance.

Figure 7:
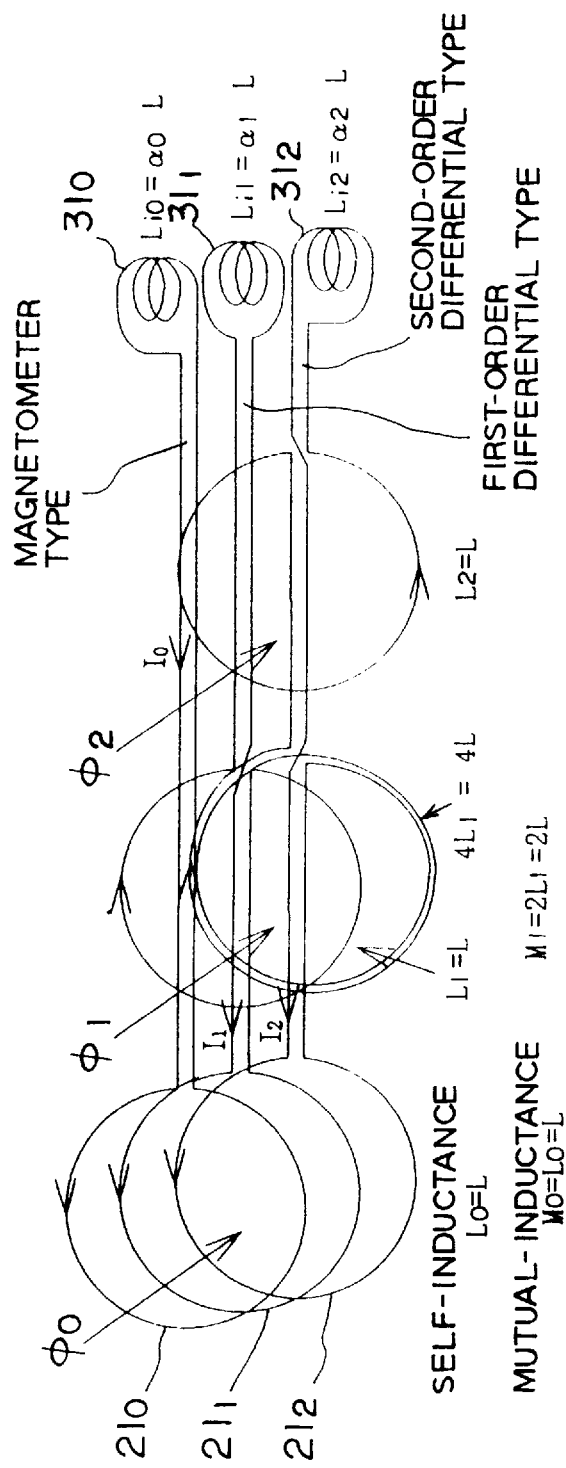
FIG. 7 is a diagram for explaining the connected states of pickup coils and input coils in the first embodiment.
Figure 8:
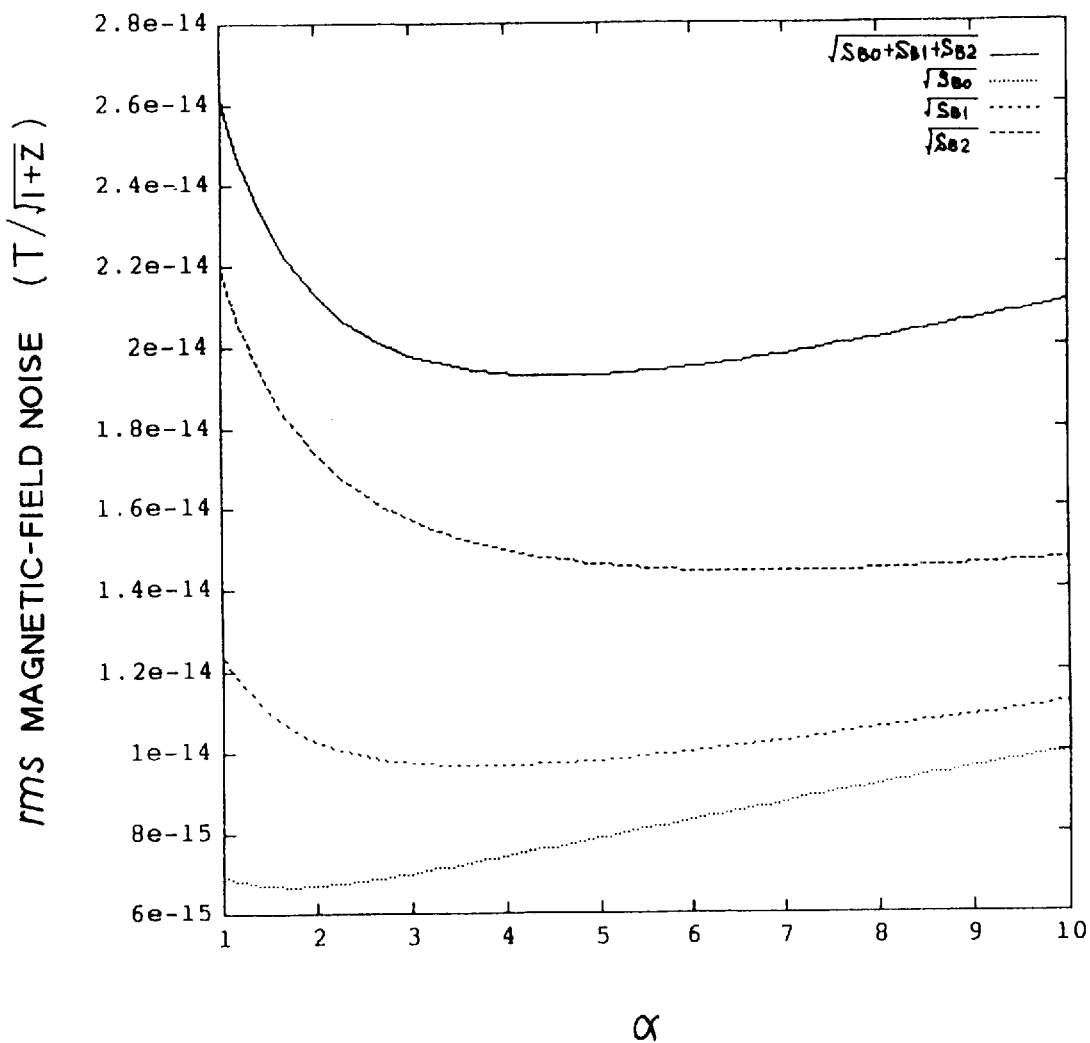
FIG. 8 is a graph showing the results of simulation performed for setting correction coefficients used to remove the influence of crosstalk among pickup coils.

FIG. 7 shows models of pickup coils $21_0$, $21_1$, and $21_2$ and input coils $31_0$, $31_1$, and $31_2$ included in each of the SQUID circuits $23_1$ to $23_{3n}$. Assuming that magnetic fluxes $\phi_0$, $\phi_1$, and $\phi_2$ applied to the pickup coils are equal to magnetic fluxes induced by screening currents $I_0$, $I_1$, and $I_2$, the inductance of one loop is L, the coupling coefficient among the loops located at the same position is 1, and the inductances of the input coils are $L_{i0}=\alpha_0 L$, $L_{i1}=\alpha_1 L$, and $L_{i2}=\alpha_2 L$ (where $\alpha_0$, $\alpha_1$, and $\alpha_2$ are ratios between the inductances $L_{i0}$, $L_{i1}$, and $L_{i2}$ and the inductance L of each loop, respectively), the magnetometer output ($\Phi_0=\phi_0$), the first-order differential output ($\Phi_1=\phi_0{-}_1$), and the second-order differential output $\Phi_2=\phi_0-2\phi_1+\phi_2$ are expressed as follows:

$$\begin{pmatrix} \phi_0 \\ \phi_1 \\ \phi_2 \end{pmatrix} = L \begin{pmatrix} 1+a_0 & 1 & 1 \\ 1 & 2+a_1 & 3 \\ 1 & 3 & 6+a_2 \end{pmatrix} \begin{pmatrix} I_0 \\ I_1 \\ I_2 \end{pmatrix} \quad (1)$$

where $\alpha_0$, $\alpha_1$, and $\alpha_2$ become correction coefficients used to compensate for the influence of crosstalk. Magnetic fluxes $\phi_{e0}$, $\phi_{e1}$, and $\phi_{e2}$ applied to the SQUID rings are expressed as follows:

$$\phi_{e0} = k_s \sqrt{a_0} \sqrt{LL_s}\, I_0 \quad (2)$$

$$\phi_{e1} = k_s \sqrt{a_1} \sqrt{LL_s}\, I_1$$

$$\phi_{e2} = k_s \sqrt{a_2} \sqrt{LL_s}\, I_2$$

where $L_s$ is the inductance of each SQUID ring and $k_s$ is a coupling coefficient relative to an input coil. The expressions (1) and (2) provide the following expression:

$$\begin{pmatrix} \phi_0 \\ \phi_1 \\ \phi_2 \end{pmatrix} = \frac{1}{k_s}\sqrt{\frac{L}{L_s}} \begin{pmatrix} \frac{1+a_0}{\sqrt{a_0}} & \frac{1}{\sqrt{a_1}} & \frac{1}{\sqrt{a_2}} \\ \frac{1}{\sqrt{a_0}} & \frac{2+a_1}{\sqrt{a_1}} & \frac{3}{\sqrt{a_2}} \\ \frac{1}{\sqrt{a_0}} & \frac{3}{\sqrt{a_1}} & \frac{6+a_2}{\sqrt{a_2}} \end{pmatrix} \begin{pmatrix} \phi_{e0} \\ \phi_{e1} \\ \phi_{e2} \end{pmatrix} \quad (3)$$

According to the expression (3), the magnetometer output, first-order differential output, and second-order differential output can be derived from the outputs of the channels (the outputs are proportional to the magnetic fluxes $\phi_{e0}$, $\phi_{e1}$, and $\phi_{e2}$ interlinked with SQUID rings) affected by the influence of crosstalk.

When a noise stemming from a SQUID or an amplifier in the first stage is converted into a thus-calculated magnetic filed, a magnetic-field noise $(S_{B0})^{1/2}$ in the magnetometer output, a magnetic-field noise $(S_{B1})^{1/2}$ in the first-order differential output, and a magnetic-field noise $(S_{B2})^{1/2}$ in the second-order differential output are expressed as follows:

$$\sqrt{S_{B0}} = \frac{\sqrt{S_\phi}}{A_p k_s} \sqrt{\frac{L}{L_s}} \sqrt{\frac{(1+a_0)^2}{a_0} + \frac{1}{a_1} + \frac{1}{a_2}} \quad (4)$$

$$\sqrt{S_{B1}} = \frac{\sqrt{S_\phi}}{A_p k_s} \sqrt{\frac{L}{L_s}} \sqrt{\frac{1}{a_0} + \frac{(2+a_1)^2}{a_1} + \frac{9}{a_2}}$$

$$\sqrt{S_{B2}} = \frac{\sqrt{S_\phi}}{A_p k_s} \sqrt{\frac{L}{L_s}} \sqrt{\frac{1}{a_0} + \frac{9}{a_1} + \frac{(6+a_2)^2}{a_2}}$$

where $A_p$ is an area of one loop, and $(S_\phi)^{1/2}$ is an rms magnetic-flux noise stemming from a SQUID. The combination of $\alpha_0$, $\alpha_1$, and $\alpha_2$ for minimizing the sum of squares $S_{B0}$, $S_{B1}$, and $S_{B2}$ of $(S_{B0})^{1/2}$, $(S_{B1})^{1/2}$, and $(S_{B2})^{1/2}$ is provided as follows:

$$\alpha_0=\sqrt{3}, \alpha_1=\sqrt{14}, \alpha_2=\sqrt{46} \quad (5)$$

Values approximate to these values should preferably be adopted. Slight deviations from the values cause no problem. For example, the same value may be assigned to $\alpha_0$, $\alpha_1$, and $\alpha_2$ respectively. As long as the value of $\alpha_0=\alpha_1=\alpha_2$ ranges from 2 to 8, a decrease in sensitivity is not so significant (See FIG. 8). When the same value is assigned to $\alpha_0$, $\alpha_1$, and $\alpha_2$ respectively, it should preferably range from 2 to 8. Incidentally, the value of $\alpha_0=\alpha_1=\alpha_2$ for minimizing the sum of $S_{B0}$ and $S_{B1}$ and $S_{B2}$ is $(21)^{1/2}$.

This embodiment has been described by taking for instance a pickup coil made by combining magnetometer type, first-order differential type, and second-order differential type pickup coils. For any other combination, an expression for compensating for crosstalk can be drawn out using the same method. An optimal ratio in inductance of the pickup coils $21_0$, $21_1$, and $21_2$ and the input coils $31_0$, $31_1$, and $31_2$ which minimizes crosstalk; that is, optimal correction coefficients $\alpha_0$, $\alpha_1$, and $\alpha_2$ can be calculated using the same method.

The processing in FIG. 6 will be described. The computer 26A reads detection signals proportional to magnetic fluxes $\phi_{e0}$, $\phi_{e1}$, and $\phi_{e2}$ that have been digitized by the A/D converters $25_1$ to $25_{3n}$ associated with the detection channels (step S1 in FIG. 6). The computer 26A then reads the correction coefficients $\alpha(\alpha_0, \alpha_1, \text{ and } \alpha_2)$ for minimizing the influence of crosstalk among the pickup coils arranged as mentioned above, which are pre-set as mentioned above, from a built-in memory to a work area (step S2). The expression (3) is then used to calculate the magnetometer output $\Phi_0$ of the magnetometer type pickup coil $21_0$, the first-order differential output $\Phi_1$ of the first-order differential type pickup coil 211, or the second-order differential output $\Phi_2$ of the second-order differential type pickup coil $21_2$ for each detection channel (step S3).

Thereafter, the computer 26A inferably computes a distribution of current sources three-dimensionally or inferably computes a single current dipole or a plurality of current dipoles according to a solution such as a read field matrix method, conjugate directions method, quasi-Newton's method, or conjugate gradients method. At this step, identifying in the depth direction the distribution of current sources or current dipoles is executed concurrently (step S4). The results of inference are output to an output unit included in the workstation 26 (step S5).

Figure 9:
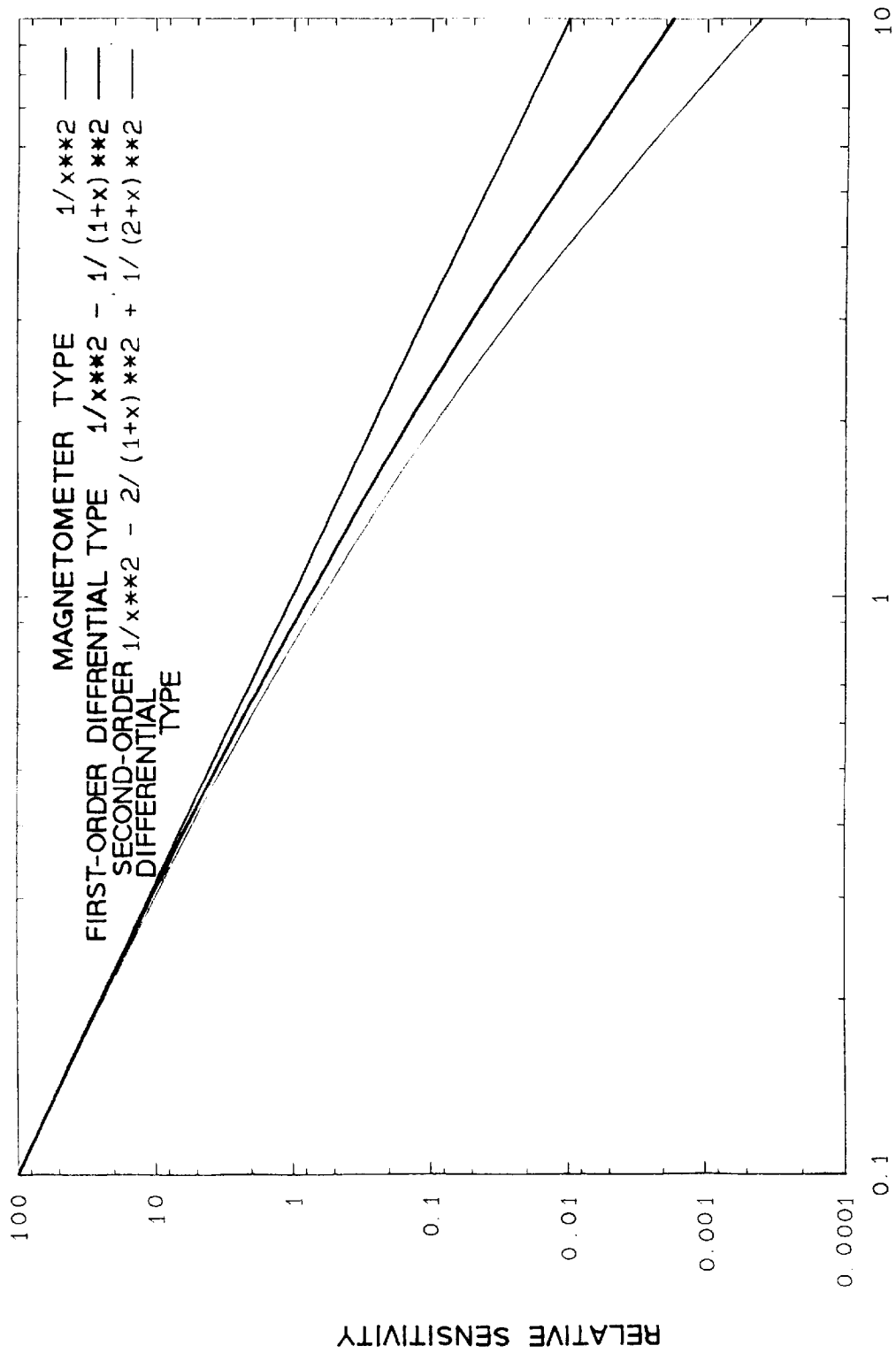
FIG. 9 is a graph relatively expressing the depth of a current source in a living body and the change in sensitivity of a pickup coil in relation to pickup coils that are mutually different in terms of the order of a differential.

FIG. 9 shows the relationship between the distance to a current source and the sensitivity of a pickup coil in relation to three types of pickup coils for providing differentials of different orders and being employed in the first embodiment. The axis of abscissae denotes distances of current sources measured with a loop close to a living body relative to a base line regarded as 1. The axis of ordinates denotes sensitivity levels of pickup coils for providing differentials of different orders relative to the sensitivity level of the magnetometer type pickup coil regarded as 1 with the distance of a current source regarded as 1. As shown in the graph, the change in sensitivity dependent on the distance of a current source is different among the orders of differentials provided by the pickup coils. Current sources at different depths can therefore be identified by employing a plurality of pickup coils that are mutually different in the order of a differential.

As mentioned above, in this embodiment, the pickup coils $21_0$, $21_1$, and $21_2$ for providing differentials of different orders are combined for each measurement point. For inferring distributed currents, the problem that the distribution of current sources is inferred to lie at a shallower position than it actually does can be solved. Furthermore, for inferring a plurality of current dipoles located at different depths, since dipoles at deeper positions can be distinguished from those at shallower positions, the current dipoles at deeper positions can be inferred accurately.

Figure 10:
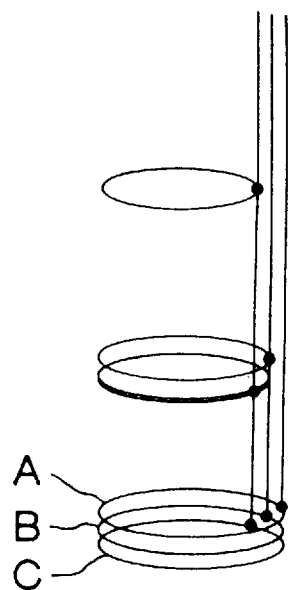
FIG. 10 shows a model in which three types of pickup coils are arranged at the same measurement point.
Figure 11:
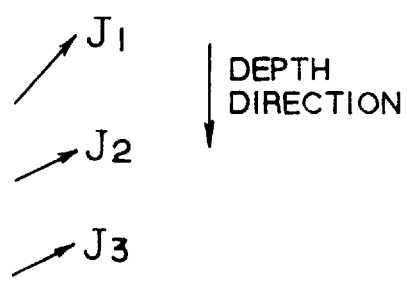
FIG. 11 shows a model in which three types of current dipoles are arranged in a depth direction.

The fact that depths of current sources can be recognized by employing a plurality of pickup coils for providing differentials of different orders will be described in conjunction with a one-dimensional model for brevity's sake. FIG. 10 shows the arrangement of three pickup coils that are mutually different in the order of a differential and current sources. The three pickup coils A, B, and C are arranged at the same measurement point and detect magnetic fields generated by three current dipoles located at different depths. A magnetic flux to be detected by a magnetometer type pickup coil shall be $f_0(J)$. J denotes a vector composed by arranging longitudinally (depth direction) moments $J_1$, $J_2$, and $J_3$ of the three current dipoles fixed at the positions shown in FIG. 11. Likewise, the magnetic flux detected by a first-order differential type pickup coil shall be $f_1(J)$ and the magnetic flux detected by a second-order differential type pickup coil shall be $f_2(J)$. Each of $f_0$, $f_1$, and $f_2$ is expressed as a sum of magnetic fields originating from each current source. The following simultaneous linear equation is therefore established:

$$\begin{pmatrix} f_0 \\ f_1 \\ f_2 \end{pmatrix} = \begin{pmatrix} f_{01} & f_{02} & f_{03} \\ f_{11} & f_{12} & f_{13} \\ f_{21} & f_{22} & f_{23} \end{pmatrix} \begin{pmatrix} J_1 \\ J_2 \\ J_3 \end{pmatrix}$$

where $f_{oi}$ (i=1, 2, or 3) denotes a magnetic field induced by an i-th current dipole (of a unit size) and detected by the magnetometer type pickup coil, and $f_{1i}$ or $f_{2i}$ denotes the magnitude of a magnetic field detected by the first-order differential type or second-order differential type pickup coil. Since the relationship between the depth of a current source and the sensitivity of a pickup coil (depth-vs.-sensitivity curve) is linearly independent among the three kinds of pickup coils, the simultaneous linear equation is regular and has only one solution. By solving the simultaneous linear equation, therefore, the magnitudes $J_1$, $J_2$, and $J_3$ of three kinds of current sources at different depths can be derived from the values of magnetic fields detected by the three types of pickup coils. If a plurality of pickup coils of a single type are arranged at the same measurement point as they conventionally are, since the same depth-vs.-sensitivity curve characterizes the plurality of pickup coils, the simultaneous linear equation becomes singular. The magnitudes of current sources at different depths cannot be determined.

For brevity's sake, a general idea has been described from a one-dimensional viewpoint. The same applies to the case like this embodiment in which measurement points are arranged on a curved surface. When pickup coils characteristic of different depth-vs.-sensitivity curves are arranged, the linear independence of a governing equation defining the relationship between a current source and a magnetic field to be measured is intensified. Consequently, the problem that when the three-dimensional distribution of current sources is to be inferred, the inferred distribution of current sources tends to be found at a shallower position or the problem that when a plurality of current sources at different depths are to be inferred, current sources at deeper positions cannot be inferred accurately can be alleviated. This effect results from the arrangement of pickup coils characteristic of different depth-vs.-sensitivity curves, and can be exerted even when the conventionally-adopted method of inferring current sources is employed. Of course, a single current dipole can be accurately inferred, as usually, in terms of its three-dimensional position, size, and orientation.

In the aforesaid embodiment, three types of pickup coils; magnetometer type, first-order differential type, and second-order differential type pickup coils are combined and arranged for each measurement point. The combination of coils is not necessarily limited to this one. Alternatively, a combination of first-order differential type or second-order differential type coils alone, a combination of first-order differential type, second-order differential type, and third-order differential type coils, or any other combination will also do.

Second Embodiment

The second embodiment of the present invention will be described in conjunction with FIGS. 12 and 13.

A biomedical magnetic field measuring apparatus in accordance with this embodiment is implemented in a dc-SQUID fluxmeter like that of the first embodiment. The overall configuration is substantially identical to that shown in FIG. 4. A difference lies in a plurality of pickup coil units $40_1$ to $40_n$ in a pickup coil array 10.

Figure 12:
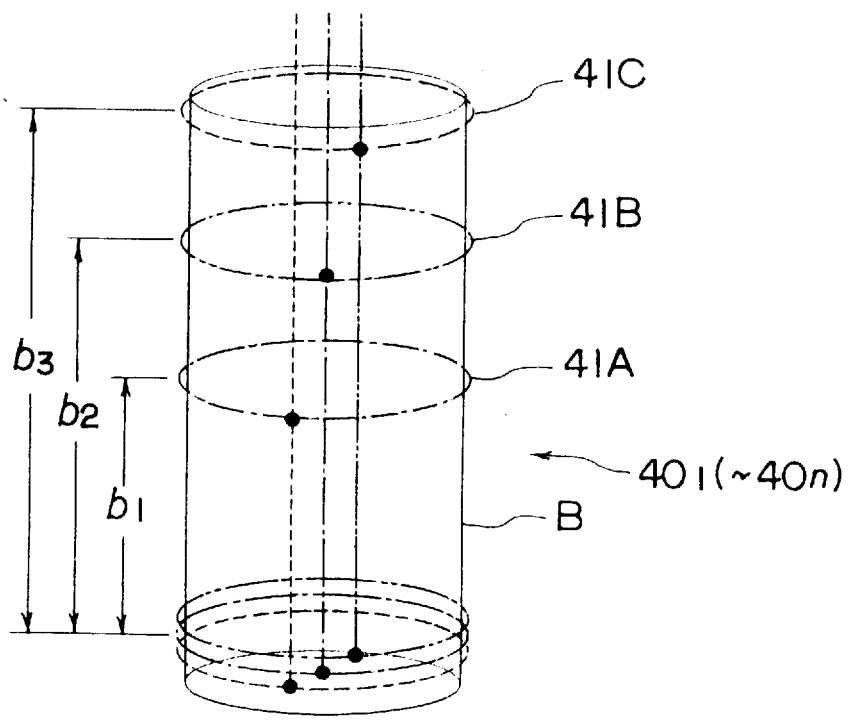
FIG. 12 shows a model of a pickup coil employed in a biomedical magnetic field measuring apparatus in accordance with the second embodiment of the present invention.

To be more specific, each of the pickup coil units $40_1$ to $40_n$ in this embodiment is, as shown in FIG. 12, composed of three first-order differential type pickup coils 41A, 41B, and 41C which have different base lines $b=b_1<b_2<b_3$ and are wound about the same bobbin B so that loops close to a living body can be superposed on one another. The pickup coil units $40_1$ to $40_n$ are, similarly to those in FIG. 5, arranged along a two-dimensional coil arrangement surface curved within a Dewar 22 and number in a given value. Thus, the first-order differential type pickup coils 41A, 41B, and 41C having three kinds of base line values and providing differentials of the same order are arranged for each of measurement points determined with the arranged positions of the pickup coil units $40_1$ to $40_n$.

In the biomedical magnetic field measuring apparatus having a dc-SQUID fluxmeter, the workstation infers magnetic sources by performing the same processing as that described in FIG. 6. Even in the second embodiment, since the coils of each of the pickup coil units $40_1$ to $40_n$ are mutually close, the influence of crosstalk is inevitable. Compensation for the influence is therefore carried out. How to set correction coefficients used for this compensation will be described below.

Assume that the inductances of loops close to a living body and of loops away from the living body are the same or L. Providing a coupling coefficient is 1, the mutual inductance of the three loops close to the living body is L. The mutual inductance of loops away from the living body is assumed to be 0. The magnetic fluxes $\phi_0$, $\phi_1$, and $\phi_2$ to be applied externally to the pickup coils 41A, 41B, and 41C are expressed similarly to those in the first embodiment as follows:

$$\begin{pmatrix} \Phi_0 \\ \Phi_1 \\ \Phi_2 \end{pmatrix} = \frac{1}{k_s} \sqrt{\frac{L}{L_s}} \begin{pmatrix} \frac{1+a_0}{\sqrt{a_0}} & \frac{1}{\sqrt{a_1}} & \frac{1}{\sqrt{a_2}} \\ \frac{1}{\sqrt{a_0}} & \frac{1+a_1}{\sqrt{a_1}} & \frac{1}{\sqrt{a_2}} \\ \frac{1}{\sqrt{a_0}} & \frac{1}{\sqrt{a_1}} & \frac{1+a_2}{\sqrt{a_2}} \end{pmatrix} \begin{pmatrix} \phi_{e0} \\ \phi_{e1} \\ \phi_{e2} \end{pmatrix} \quad (6)$$

The above expression provides a signal $\Phi_0$ corresponding to a magnetometer output, a signal $\Phi_1$ corresponding to a first-order differential output, and a signal $\Phi_2$ corresponding to a second-order differential output, which are deprived of the influence of crosstalk which has affected the detection signals proportional to the magnetic fluxes $\phi_{e0}$, $\phi_{e1}$, and $\phi_{e2}$ applied to the SQUID rings.

When a noise stemming from an SQUID or an amplifier in the first stage is converted into a magnetic field, a magnetic-field noise $(S_{B0})^{1/2}$ in the magnetometer output, a magnetic-field noise $(S_{B1})^{1/2}$ in the first-order differential output, and a magnetic-field noise $(S_{B2})^{1/2}$ in the second-order differential output are expressed as follows:

$$\sqrt{S_{B0}} = \frac{\sqrt{S_\phi}}{A_p k_s} \sqrt{\frac{L}{L_s}} \sqrt{\frac{(1+a_0)^2}{a_0} + \frac{1}{a_1} + \frac{1}{a_2}}$$

$$\sqrt{S_{B1}} = \frac{\sqrt{S_\phi}}{A_p k_s} \sqrt{\frac{L}{L_s}} \sqrt{\frac{1}{a_0} + \frac{(1+a_1)^2}{a_1} + \frac{1}{a_2}}$$

$$\sqrt{S_{B2}} = \frac{\sqrt{S_\phi}}{A_p k_s} \sqrt{\frac{L}{L_s}} \sqrt{\frac{1}{a_0} + \frac{1}{a_1} + \frac{(1+a_2)^2}{a_2}} \quad (7)$$

where $A_p$ denotes an area of one loop, and $(S_\Phi)^{1/2}$ denotes an rms magnetic-flux noise stemming from a SQUID. The $(S_{B0})^{1/2}$, $(S_{B1})^{1/2}$, and $(S_{B2})^{1/2}$ values are minimized when $\alpha_0 = \alpha_1 = \alpha_2 = (3)^{1/2}$ is established. In this embodiment, therefore, the inductance of each input coil should be set to a larger value (in the order of $L_{i0} = L_{i1} = L_{i2} = (3)^{1/2}L$) than a normally-designed value ($L_i = L$).

Figure 13:
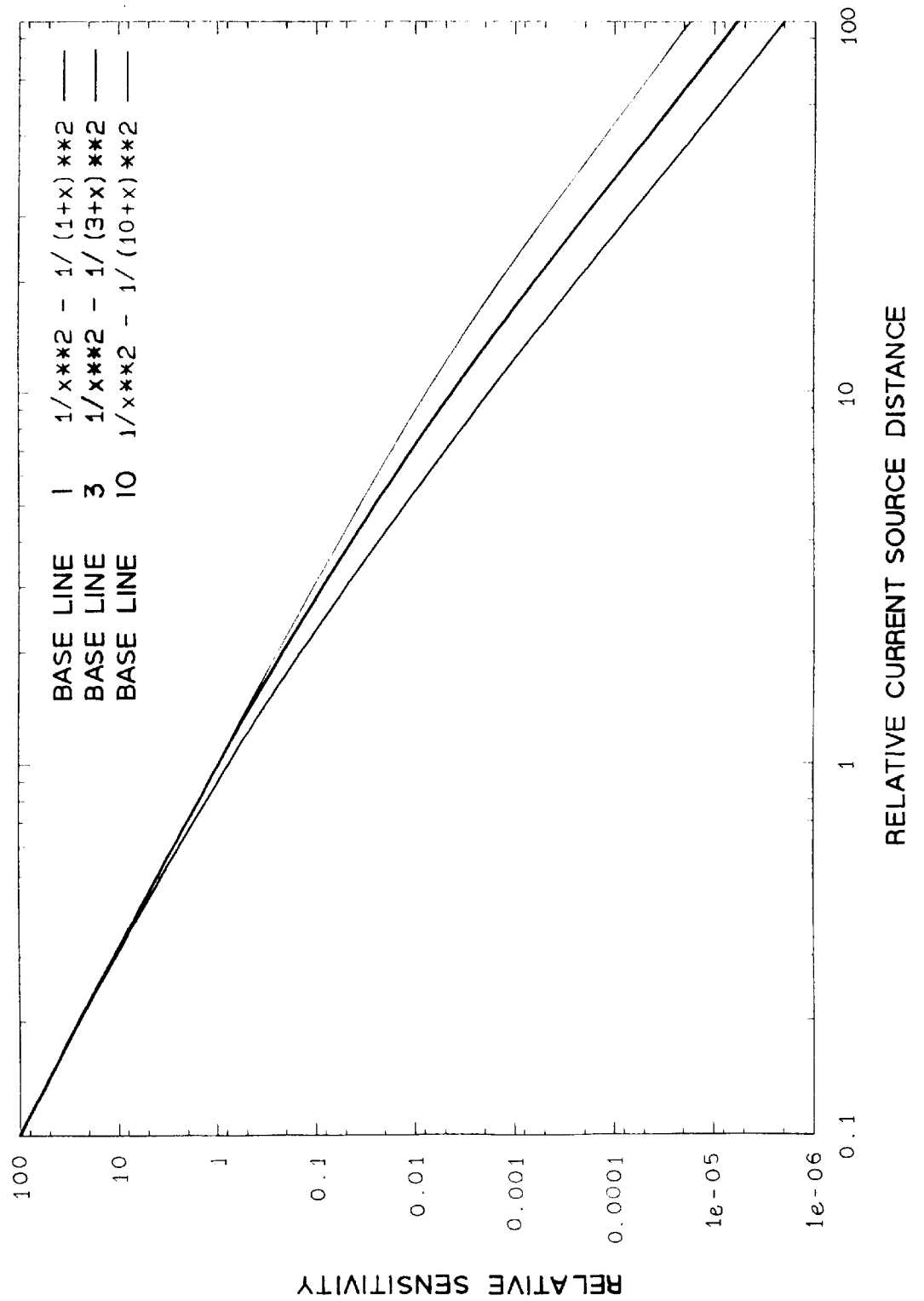
FIG. 13 is a graph relatively expressing the depth of a current source in a living body and the change in sensitivity of a pickup coil in relation to pickup coils that are mutually different in terms of the base line.

FIG. 13 shows the relationship between the distance of a current source and the sensitivity of a pickup coil in relation to pickup coils having three kinds of base lines and being employed in the second embodiment. The three kinds of base lines of the pickup coils are 1, 3, and 10 for instance. The axis of abscissae denotes distances of current sources from a loop close to a living body relative to the shortest base line regarded as 1. The axis of ordinates denotes sensitivity levels of the three types of pickup coils relative to the sensitivity level of a magnetometer type pickup coil regarded as 1 with the distance of a current source regarded as 1. As shown in the graph, the change in sensitivity dependent on the distance of a current source is different among the base lines of the pickup coils. When a plurality of pickup coils having different base lines are employed, therefore, current sources at different depths can be distinguished from one another by performing the same processing as that in the first embodiment.

Similarly to the first embodiment, this embodiment in which pickup coils having different base lines are combined can alleviate the problem that when distributed currents are to be inferred, the inferred distribution of current sources is located at a shallower position than it actually is. Furthermore, when a plurality of current dipoles at different depths are to be inferred, since dipoles at deeper positions can be distinguished from dipoles at shallower positions, the dipoles at the deeper positions can be inferred accurately.

In this embodiment, three first-order differential pickup coils having different base lines are arranged at the same measurement point. Alternatively, two pickup coils having different base lines or four or more pickup coils having different base lines may be arranged at the same measurement point (bobbin). A plurality of second-order or higher-order differential type pickup coils having different base lines may be arranged at the same measurement point.

Third Embodiment

Figure 14:
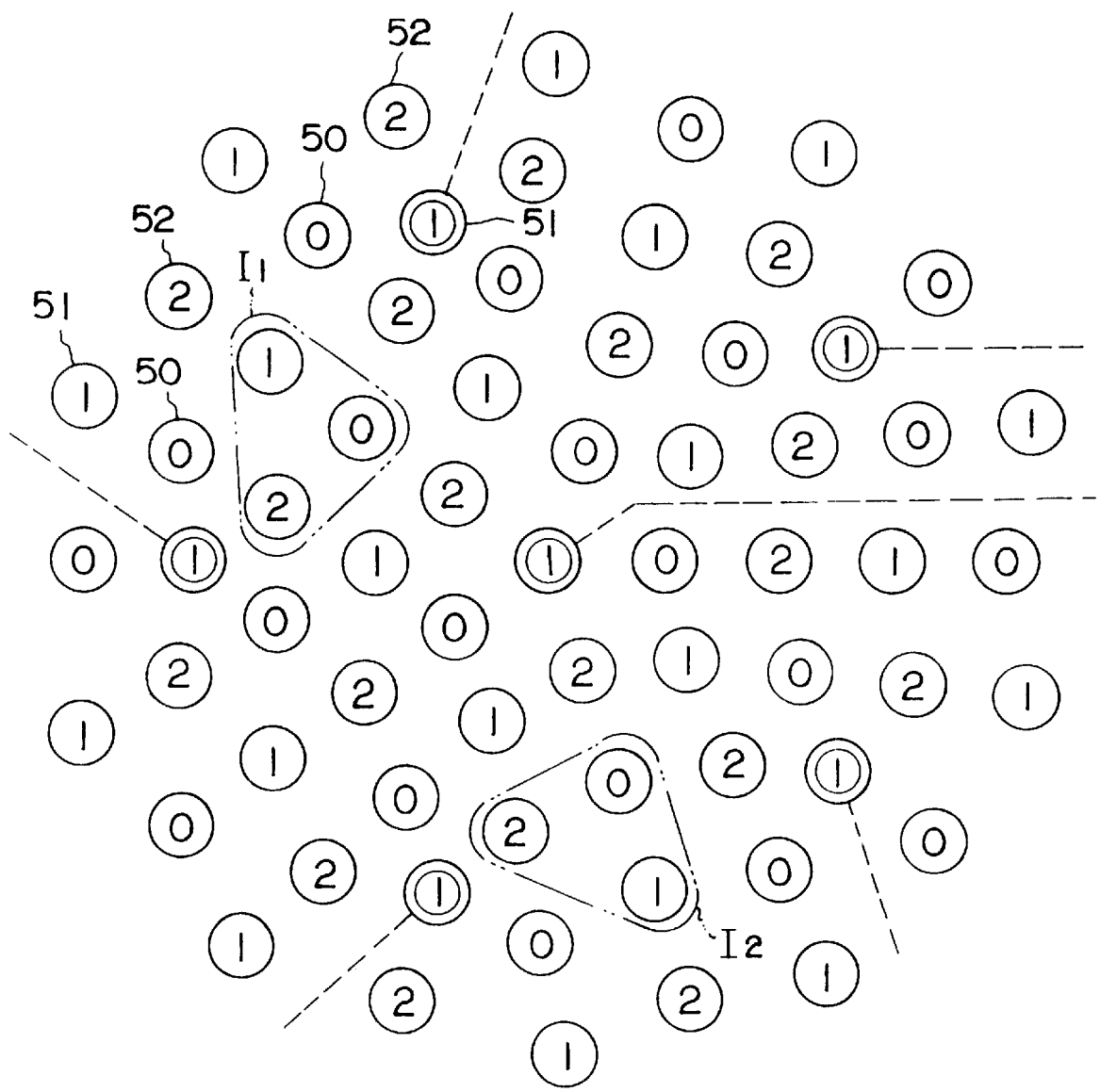
FIG. 14 shows the arrangement of models of pickup coils employed in a biomedical magnetic field measuring apparatus in accordance with the third embodiment of the present invention.

The third embodiment of the present invention will be described in conjunction with FIG. 14. A pickup coil array for a biomedical magnetic field measuring apparatus of this embodiment has pickup coils for providing differentials of different orders arranged at different measurement points. For example, the layout shown in FIG. 14 is adopted. The layout of this and the later-described embodiments is derived from a manner of quasi-regular polyhedron.

Shown in FIG. 14 is an example in which a plurality of magnetometer type pickup coils 50 (indicated with encircled 0 in FIG. 14), a plurality of first-order differential type pickup coils 51 (indicated with encircled 1 in FIG. 14), and a plurality of second-order differential type pickup coils 52 (indicated with encircled 2 in FIG. 14) are arranged independently. The pickup coils 50, 51, and 52 are arranged while being wound about separate bobbins. Each circle in FIG. 14 indicate one measurement point. This arrangement is intended exclusively for measurement of the head. In principle, the pickup coils are arranged on a curved surface covering the head. In the drawing, for brevity's sake, the curved surface is developed into a plane and the measurement points are drawn on the plane.

This layout features that pickup coils at three adjoining measurement points (See, for example, virtual lines 11 and 12 in the drawing) are of different types. Since pickup coils at adjoining measurement points are thus of different types, three types of pickup coils can be arranged uniformly. This is advantageous. However, each of measurement points indicated with a double circle has only five adjoining measurement points (all the other measurement points have six adjoining points). In a region over a dashed line, therefore, all adjoining measurement points are not occupied by different types of pickup coils. However, the number of such regions (over dashed lines) is made as small as possible. As a whole, three types of pickup coils that are mutually different in the order of a differential can be considered to be arranged substantially uniformly. Consequently, the same effect and advantage as those of the first embodiment can be provided.

This embodiment features that pickup coils, which are different in the order of a differential, are arranged at respective measurement points. As for the orders of differentials provided by pickup coils, aside from those mentioned above, various combinations such as three kinds of orders; the first order, second order, and third order or four kinds of orders; the zero order, first order, second order, and third order are conceivable.

Fourth Embodiment

The fourth embodiment of the present invention will be described in conjunction with FIG. 15. A pickup coil array for a biomedical magnetic field measuring apparatus in accordance with this embodiment has pickup coils having different base lines arranged at different measurement points. For example, the layout shown in FIG. 15 is adopted.

Figure 15:
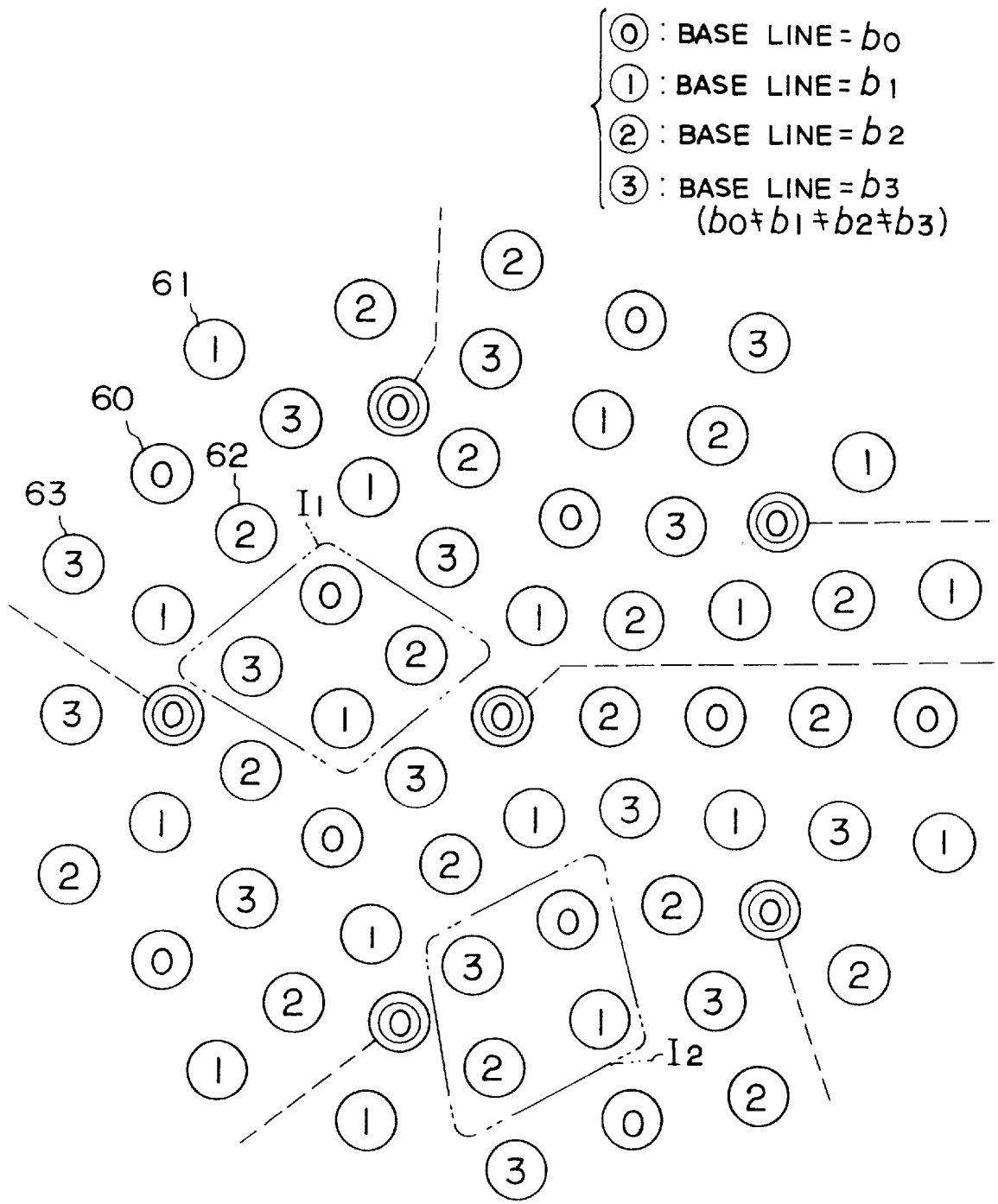
FIG. 15 shows the arrangement of models of pickup coils employed in a biomedical magnetic field measuring apparatus in accordance with the fourth embodiment of the present invention.

Shown in FIG. 15 is an example in which pickup coils having four kinds of base lines; a plurality of first-order differential type pickup coils 60 having a base line $b_0$ (indicated with encircled 0 in FIG. 15), a plurality of first-order differential type pickup coils 61 having a base line $b_1$ (indicated with encircled 1 in FIG. 15), a plurality of first-order differential type pickup coils 62 having a base line $b_2$ (indicated with encircled 2 in FIG. 15), and a plurality of first-order differential type pickup coils 63 having a base line $b_3$ (indicated with encircled 3 in FIG. 15) are arranged independently. The pickup coils 60, 61, 62, and 63 are arranged while being wound about respective bobbins. Each circle in FIG. 15 indicates one measurement point. This apparatus is intended for measurement of the head. In principle, the pickup coils are arranged on a curved surface covering the head. In the drawing, for brevity's sake, the curved surface is developed into a plane, and the measurement points are drawn on the plane.

This layout features that pickup coils at four adjoining measurement points (adjoining measurement points defining a diamond. See, for example, virtual lines $I_1$ and $I_2$ in the drawing) have different base lines. Since pickup coils at four adjoining measurement points thus have different base lines, four types of pickup coils can be arranged uniformly. This is advantageous. However, each of measurement points indicated with a double circle has only five adjoining measurement points (all the other measurement points have six adjoining measurement points). In a region over a dashed line, therefore, all adjoining measurement points are not occupied by pickup coils having different base lines. However, the number of such regions over dashed lines are made as small as possible. As a whole, four types of pickup coils having different base lines can be considered to be arranged substantially uniformly. Consequently, the same effect and advantage as those of the second embodiment can be provided.

This embodiment features that pickup coils having different base lines are arranged at respective measurement points. The number of different base lines to be combined is four in the foregoing example. Aside from this, the number of different base lines to be combined may be 2, 3, 4, or 5 or larger. Arranging three types of pickup coils having different base lines should be carried out in the same manner as that in the third embodiment shown in FIG. 14.

Figure 16:
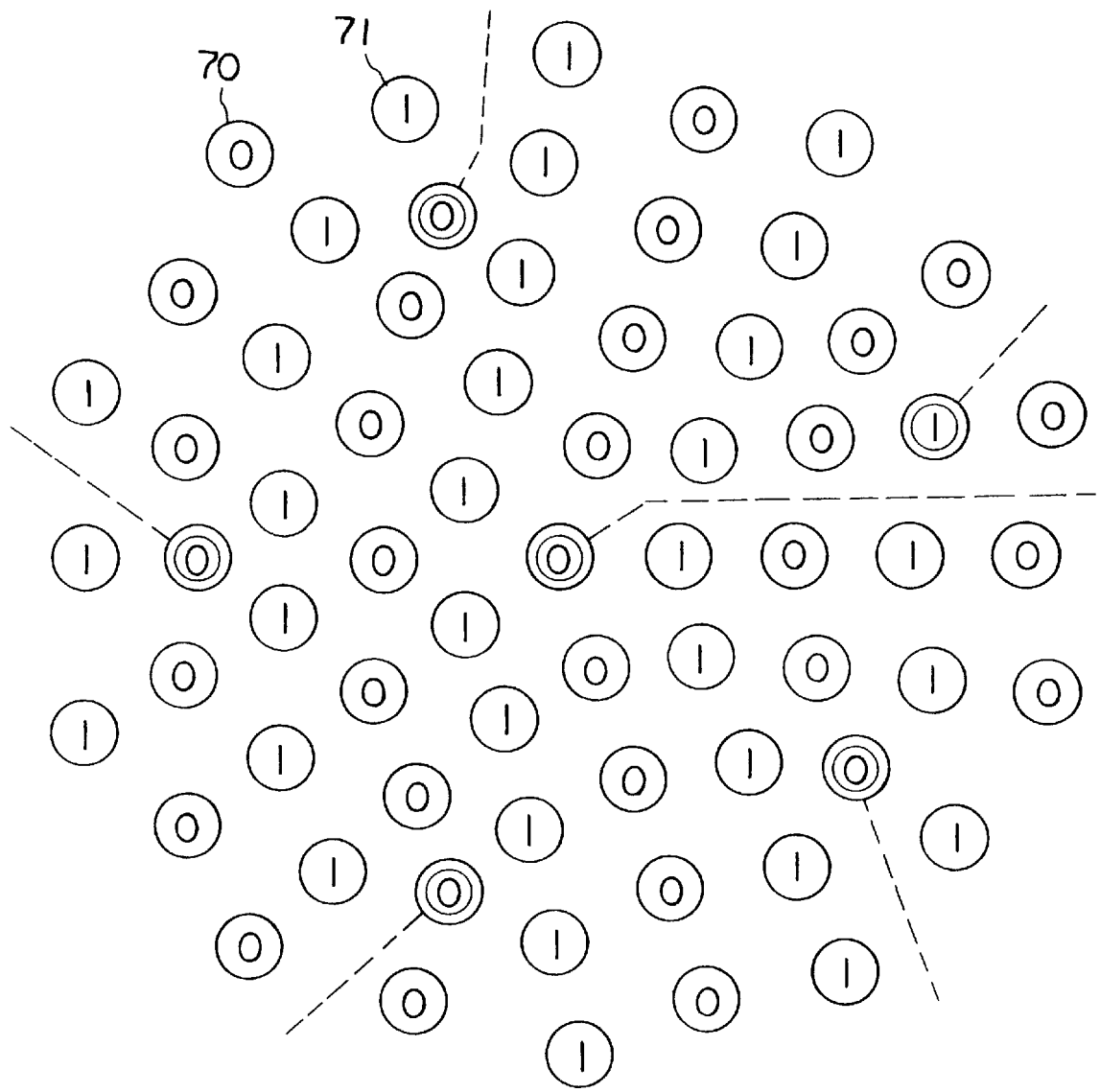
FIG. 16 shows the arrangement of models of pickup coils employed in a variant of the fourth embodiment.
Figure 17:
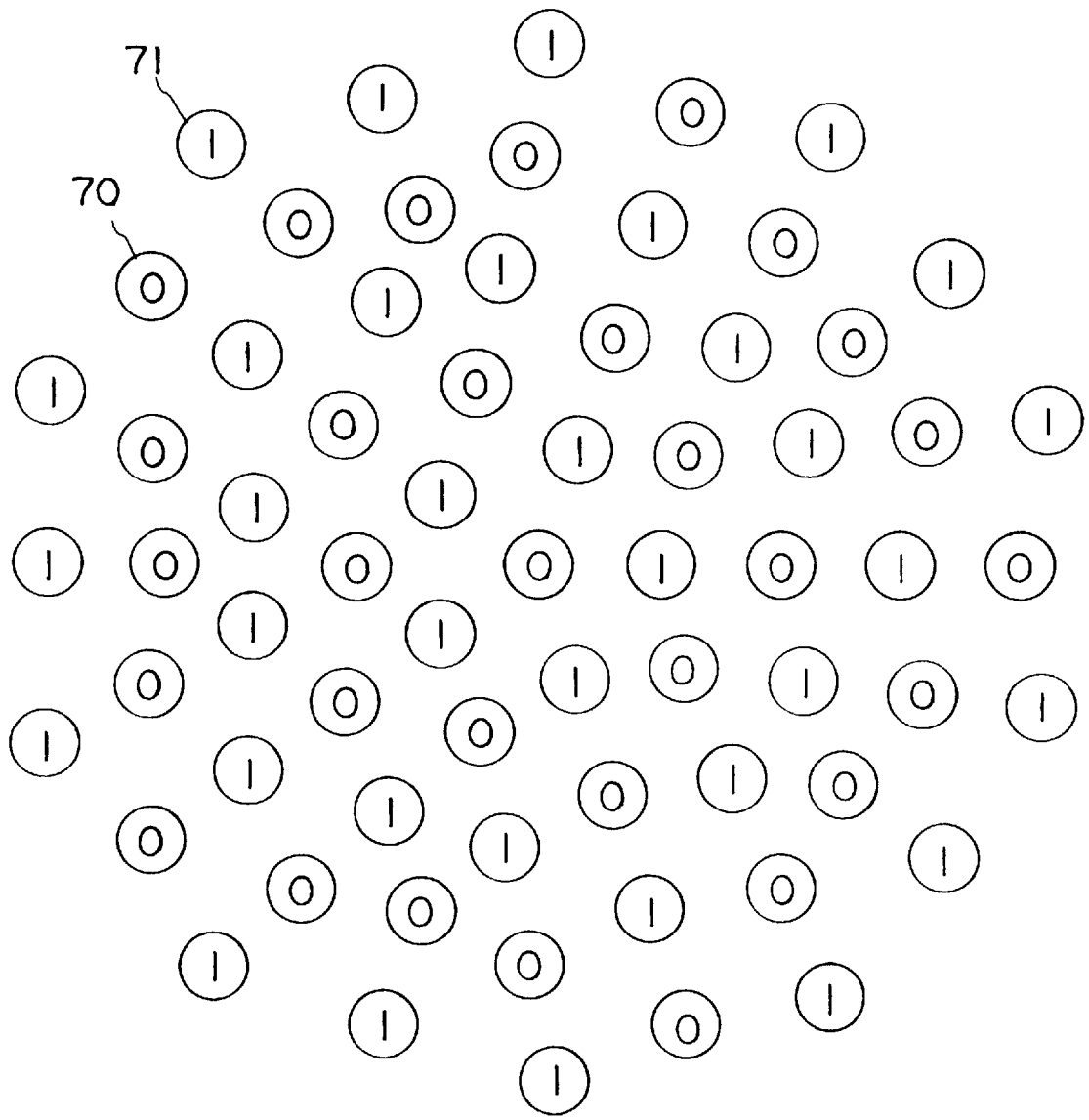
FIG. 17 shows the arrangement of models of pickup coils employed in another variant of the fourth embodiment.

Variants in which two types of pickup coils 70 and 71 having different base lines $b_0$ and $b_1$ are arranged at different measurement points are shown in FIGS. 16 and 17. In FIG. 16, pickup coils having the same base line are arranged substantially linearly. Two types of pickup coils having different base lines are lined alternately in a direction substantially perpendicular to this line. In FIG. 17, two types of pickup coils having different base lines are alternately arranged substantially concentrically.

Fifth Embodiment

The fifth embodiment of the present invention will be described in conjunction with FIGS. 18A to 18C. In this embodiment, pickup coils providing differentials of different orders and pickup coils having different base lines are combined and arranged at the same measurement point or at different measurement points. When the combined pickup coils are arranged at the same measurement point, compensation for crosstalk among coils is carried out in the same manner as that in the first or second embodiment.

Figures 18A, 18B, 18C:
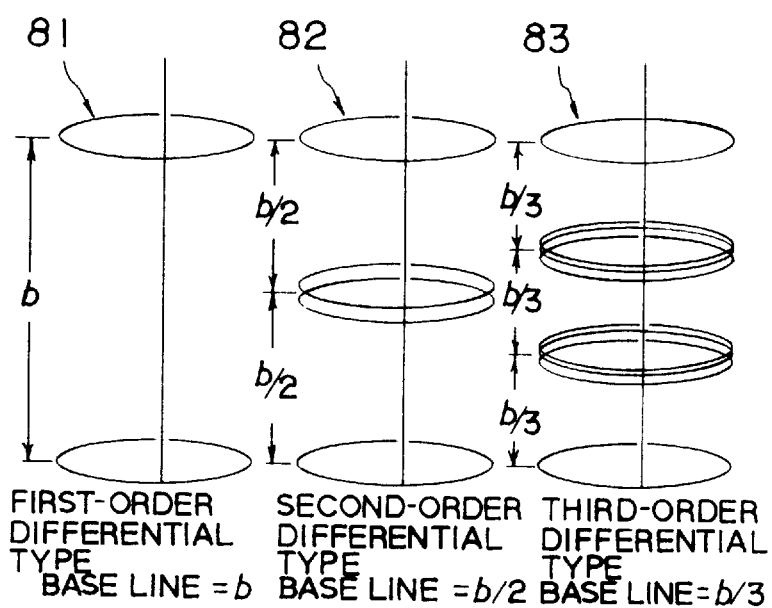
FIGS. 18A to 18C show models for explaining a plurality of types of pickup coils employed in a biomedical magnetic field measuring apparatus in accordance with the fifth embodiment of the present invention.

FIGS. 18A to 18C shows three types of pickup coils 81, 82, and 83 to be combined as an example of combination. In these examples, the first-order, second-order, and third-order differential type pickup coils 81, 82, and 83 are combined and have base lines thereof made mutually different. The higher the order of a differential is, the shorter the base line is. This setting makes it possible to make the length of a whole pickup coil unit in the axial direction thereof equal to or not longer than the base line of the first-order differential type pickup coil. Consequently, the size of a pickup coil unit can be made smaller than that in the first embodiment.

The three types of thus-configured pickup coils 81, 82, and 82 are arranged along a coil arrangement surface of a Dewar according to the layout described in conjunction with FIG. 14. Detection and data processing similar to those described previously are then carried out. Consequently, the same effect and advantages as those in the aforesaid embodiments can be provided.

In a variant, a zero-order differential type pickup coil or first-order differential type pickup coil may be offset in the axial direction. Software is used to perform signal processing equivalent to that performed by a higher-order pickup coil. This signal processing can be adapted for an inverse problem or vector processing.

As described so far, according to the present invention, a pickup coil array is made by combining a plurality of types of pickup coils that are mutually different in terms of at least one of the order of a differential and a base line. A magnetic source inferring means having a means for compensating for the influence of magnetic crosstalk among a plurality of pickup coils is included. Information acquired from a plurality of pickup coils therefore contains information on depths of magnetic sources. This results in improved resolution in the results of interference and improved sensitivity in detection in a depth direction of a living body. Since the influence of crosstalk can be compensated for, even if the number of channels is increased, an overall signal-to-noise ratio can be improved equivalently. Moreover, it can be prevented that a distribution of current sources is inferred to lie at a shallower position than it actually is. Even when a plurality of current dipoles are overlapped in a depth direction, the accuracy in inferring current sources located at deeper positions can be improved. Additionally, a single current dipole can also be inferred in high accuracy using this apparatus, if necessary. Consequently, magnetic sources can be inferred more highly accurately than they conventionally are.

For the sake of completeness it should be mentioned that the embodiment examples shown in the Figures are not definitive lists of possible embodiments. The expert will appreciate that it is possible to combine the various construction details or to supplement or modify them by measures known from the prior art without departing from the basic inventive principle.

What is claimed is:

1. A biomedical magnetic field measuring apparatus providing information of a biomedical magnetic field source residing within a living body by sensing a magnetic flux originating from the source of the living body, comprising:

a pickup coil array including at least one set of pickup coils sensing the magnetic flux in a substantially same measuring direction and being arranged set by set at a same single measuring position on a coil arrangement plane placed in the vicinity of the living body, each pickup coil in said at least one set of pickup coils having a differential order coil structure and a base line length, wherein at least one of the differential order coil structure and the base line length of each pickup coil in said at least one set of pickup coils is different than that of the remaining pickup coils of said at least one set, a plurality of circuits respectively connected to each of the pickup coils of each set and respectively equipped with a SQUID circuit and a SQUID-driving circuit for measuring the magnetic flux simultaneously sensed by each pickup coil and for outputting a signal corresponding to the sensed magnetic flux; and a unit for inferring the information based on the signals outputted by the plurality of circuits, said inferring unit comprising means for performing correction for magnetic crosstalk caused among the pickup coils of each set.

2. The apparatus of claim 1, wherein said SQUID-driving circuit is an FLL (flux locked loop) circuit driving the SQUID circuit for obtaining the signal.

3. The apparatus of claim 1, wherein said correction means comprises a computer and a memory, the computer performing processing of the correction on the signal using correction coefficients being previously set and stored in the memory.

4. The apparatus of claim 3, wherein said inferring unit comprises means for computing the information from signal results corrected by the correction means using an algorithm, the information including positional information of the sources in the measuring direction.

5. The apparatus of claim 4, wherein said computing means comprises said computer and said memory used in common with the computer used to operate the algorithm and the memory used to store therein data representing the algorithm.

6. The apparatus of claim 1, wherein said information inferred by the inferring unit consists of either one of information concerning a current dipole residing within the living body and information concerning a distribution of current sources residing within the living body.

7. The apparatus of claim 1, wherein said pickup coils of each set are different from each other in the differential order coil structure alone.

8. The apparatus of claim 7, wherein said each set of pickup coils consists of at least two of a magnetometer type pickup coil, a first-order differential type pickup coil, a second-order differential type pickup coil, and a third-order differential type pickup coil.

9. The apparatus of claim 7, wherein said pickup coils of each set are wound around a same single bobbin.

10. The apparatus of claim 1, wherein said pickup coils of each set are different from each other in the base line length alone.

11. The apparatus of claim 10, wherein said pickup coils of each set are wound around a same single bobbin.

12. The apparatus of claim 1, wherein said pickup coils of each set are different from each other in both the differential order coil structure and the base line length.

13. The apparatus of claim 1, wherein said coil arrangement plane is curved in harmony with a surface curvature of a region to be measured of the living body.

* * * * *